United States Patent [19]

Chin et al.

[11] Patent Number: 4,739,760

[45] Date of Patent: Apr. 26, 1988

[54] VEIN VALVE CUTTER APPARATUS

[75] Inventors: Albert K. Chin, Palo Alto, Calif.; Thomas J. Fogarty, 770 Welch Rd., Palo Alto, Calif. 94304

[73] Assignee: Thomas J. Fogarty, Palo Alto, Calif.

[21] Appl. No.: 871,517

[22] Filed: Jun. 6, 1986

[51] Int. Cl.⁴ .............................................. A61B 17/32
[52] U.S. Cl. ....................................... 128/305; 604/22
[58] Field of Search .................. 128/305, 303.15, 304; 604/22; 128/348.1

[56] References Cited

U.S. PATENT DOCUMENTS

| 3,837,345 | 9/1974 | Matar | 128/305 |
| 4,002,169 | 1/1977 | Cupler | 128/305 X |
| 4,207,874 | 6/1980 | Choy | 128/6 |
| 4,427,014 | 1/1984 | Bel et al. | 128/305 X |
| 4,631,052 | 12/1986 | Kensey | 128/305 X |
| 4,655,217 | 4/1987 | Reed | 128/305 |

FOREIGN PATENT DOCUMENTS

83/04174 12/1983 PCT Int'l Appl. ................. 128/305

Primary Examiner—Michael H. Thaler
Attorney, Agent, or Firm—Limbach, Limbach & Sutton

[57] ABSTRACT

A cutter for the in-situ cutting of valves within a vein. The cutter comprises a catheter having cutter fingers extending from its open distal end in an annular pattern. A sheath is selectively extensible over the fingers to shield them from inadvertent contact with the vein being treated. A fiberoptic viewer extends through the catheter to view through its open distal end.

16 Claims, 1 Drawing Sheet

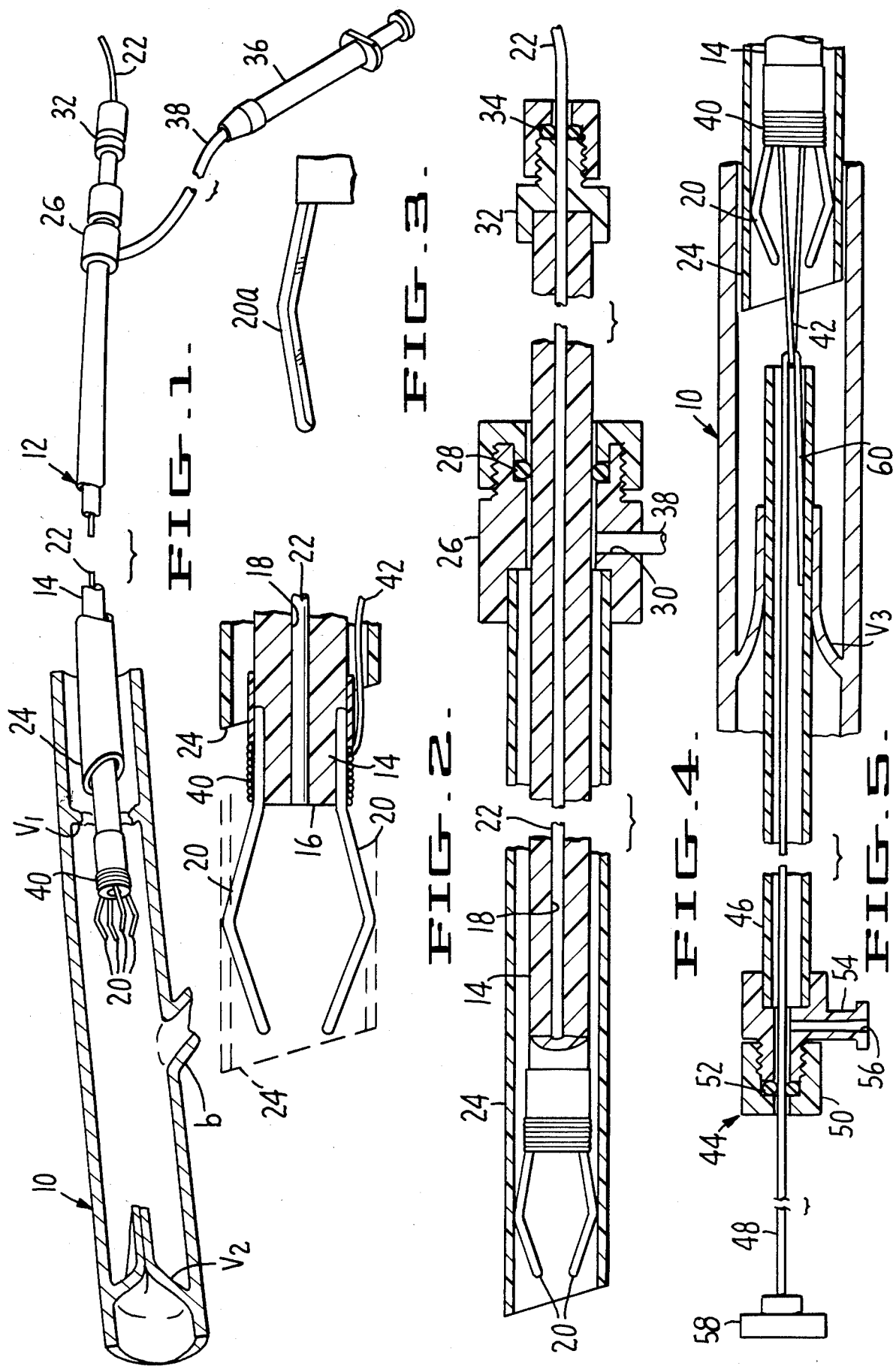

VEIN VALVE CUTTER APPARATUS

BACKGROUND OF THE INVENTION

The present invention relates to a vein valve cutter for use in disrupting vein valves during vascular reconstructive surgery. In its more particular aspects, it is concerned with a method and apparatus for use in a procedure known as in-situ saphenous vein bypass.

In the in-situ saphenous procedure, atherosclerotic occlusive disease in the femoropopliteal arterial system is bypassed with a segment of nearby saphenous vein left "in situ"; that is, undissected from its native bed. In order to use the saphenous vein as an arterial conduit, the valves of the vein must be disrupted. This allows arterial flow to proceed in a direction normally prevented by the intact valves. The saphenous vein segment, now devoid of valves, is anastamosed to the femoral artery and a distal artery, such as the tibial artery, to bypass the diseased section.

Previous efforts to achieve the in-situ disruption of the valves within a vein have included the following techniques:

1. Valve incision with a pair of tiny scissors performed through venotomies proximal the valve sites, or through side branches close to the valve sites.

2. Valve incision performed from below the valve site by passage of a valvulotome through the valve followed by incision of the leaflets upon pulling of the device back through the valve. The valvulotome is a long thin instrument with a curved hook-like cutting tip. It may be introduced in the vein being treated through a side branch.

3. Vein strippers which break the valves upon passage of the strippers in a direction against normal blood flow. Such strippers consist of one or two bullet-shaped members which are initially introduced in either antegrade or retrograde directions. One type of stripper, known as a "Cartier stripper" employs a cone-shaped stripper with a circular cutting edge around its divergent end. This type of stripper is passed through the valve apex end first in the normal direction of blood flow and then drawn back in the reverse direction to cut the valve with the circular cutting edge.

4. A more recent type of stripper somewhat related to the latter type provides a double cylinder arrangement which is passsed through the vein. The initial cylinder is blunt and the second cylinder has two cutting blades. In use, the instrument is first passed through the vein and valve to be treated in the direction of normal blood flow and then drawn back in reverse direction to draw the cutting blades of the second cylinder through the valve.

The above prior techniques involve either cutting of the valves through an open incision near the valve site, or the blind passage of a cutting or stripping device. The direct open incision method of valve cutting is tedious and time-consuming. Blind incision of valves, however, is hazardous to the vein being treated. Side branches may be caught and avulsed by the valve cutters. Endothelial damage may also result from the blind incision of valves.

SUMMARY OF THE INVENTION

The cutter of the present invention embodies a catheter having an open distal end with annularly arranged cutting fingers extending therefrom. The cutter is operable under direct visualization through a lighted fiberoptic viewer which extends through the catheter. A sheath surrounds the catheter for selective extension over the cutting fingers to shield them from undesired contact with the internal walls of a vein as the cutter is being directed to the situs of a valve to be cut. In the preferred embodiment, the cutter includes fluid infusion means to provide pulsatile flow to aid in the identity of valves through the fiberoptic scope, and close the valves during the cutting process.

A principal object of the invention is to provide an improved in-situ vein valve cutter which provides for visual viewing to locate valves and assist in the control of the cutting operation.

Another object of the invention is to provide such a cutter which employs a plurality of annularly arranged cutting fingers which assure that the valve will be effectively cut with a minimum of trauma to the vein.

Still another object of the invention is to provide such a cutter with a sheath to selectively shield the cutting fingers from contact with the vein.

Yet another object of the invention is to provide such a cutter with fluid infusion means to provide pulsatile flow during placement of the cutter to locate valves.

A further object is to provide a cutter with such fluid infusion means which may be used to apply fluid pressure to a valve during the cutting operation to maintain the valve in a closed condition during the operation.

A further object of the invention is to provide a cutter which may be drawn through a vein by pushing or pulling forces, or a combination of such forces.

The foregoing and other objects will become more apparent when viewed in light of the following detailed description and accompanying drawings.

BRIEF DESCRIPTION OF THE DRAWINGS

FIG. 1 is a perspective view of the cutter of the present invention in the process of being directed through a vein to a valve to be cut;

FIG. 2 is a cross-sectional view illustrating the distal end of the cutter, with the sheath shown in solid lines in a condition retracted to expose the cutter fingers and in phantom lines extended to shield the fingers.

FIG. 3 illustrates an alternate embodiment of the cutter fingers, wherein the fingers are formed with sharpened inward cutting edges;

FIG. 4 is a cross-sectional view, with parts thereof broken away, illustrating the internal construction of the cutter; and FIG. 5 is a cross-sectional view of the cutter within a vein, with a pulling instrument secured to the cutter to draw it through the vein under tension.

DESCRIPTION OF THE PREFERRED EMBODIMENTS

The vein shown in FIG. 1 is designated by the numeral 10 and is shown as having a first valve $v_1$ which has been cut by the instrument of the present invention and a second valve $V_2$ which is intact and in the process of being approached by the cutter. The vein shown in FIG. 5 is also designated by the numeral 10. As there shown, a third valve $v_3$ is shown in the process of having the cutter drawn thereto by the pulling instrument of the invention.

The cutter assembly of the invention is designated in its entirety by the numeral 12 and comprises: a catheter 14 having a distal end 16 and a through lumen 18 opening through the distal end; four cutting fingers 20 secured to and extending from the distal end of the catheter; an illuminated fiberoptic scope 22 extending slidably through the lumen 18 for viewing through the open distal end thereof; and, a sheath 24 telescopically received on the catheter 14 for movement relative thereto between the retracted and extended conditions shown in solid and phantom lines, respectively, in FIG. 2. A first seal block 26 is secured in sealed and concentric relationship to the sheath 24, said seal block housing an O-ring 28 in sealed slidable engagement with the catheter 14 and having an infusion port 30 in fluid communication with the annular space between the catheter 14 and the sheath 24. A second seal block 32 is sealingly secured to the proximal end of the catheter 14, said block housing an O-ring 34 in sealed slidable engagement with the fiberoptic scope 22. The assembly shown in FIG. 1 is completed by a syringe 36 connected in fluid communication with the infusion port 30 through a flexible tube 38. The syringe provides means whereby fluid pressure may be provided to the interior of a vessel within which the cutter assembly is placed.

The fiberoptic scope 22 may be of the lighted type manufactured by Edwards Laboratories of Santa Ana, Calif. In the preferred embodiment of the present invention, a scope having an outside diameter of approximately 1 mm is used. Such scopes have a central monolithic viewing strand surrounded by a plurality of peripheral illuminating strands. Although not illustrated, it should be understood that the proximal end of the scope would be secured to a suitable viewer, such as a magnifying eyepiece or video viewer.

In the illustrated embodiment, the cutting fingers 20 are secured to the distal end of the catheter 14 by adhesive and suture winding 40. Alternatively, the fingers may be molded into the catheter or attached by other means, such as brazing onto a metal insert which is attached to the catheter tip. The fingers have rounded smooth distal ends to avoid digging into the vein walls. In the embodiment of FIGS. 1, 2, 4 and 5, the fingers 20 are of cylindrical cross-section, with divergent proximal portions and convergent distal portions. This divergent convergent configuration also assures that the fingers will not dig into the vein walls. FIG. 3 shows an alternative configuration of the cutting fingers, designated 28, wherein the fingers have a cross-section with the inner side thereof in the form of a knife edge. This embodiment has the same divergent convergent configuration and rounded distal ends of the embodiment of FIGS. 1, 2, 4 and 5.

The divergent convergent configuration of the cutting fingers 20 and 28 conforms to the natural configuration of a vein valve leaflet, allowing the cutting fingers to slide to the apex of the valve and achieve complete valve incision. In the preferred embodiment, four fingers are used to help distend the vein for adequate fiberoptic scope visualization during cutting, and to assure that at least one of the cutting arms advances to the apex of each valve leaflet. Normally, there are two valve leaflets per valve.

The catheter 14 and sheath 24 may be fabricated of any suitable polymer material capable of bending to conform to the shape of a vein through which the cutter assembly is directed. Ideally, the catheter 14 should have sufficient column strength to enable it to be used in a "push mode" as shown in FIG. 1. However, in the preparation of extended lengths of vein, it may become necessary to pull the cutting assembly to cut the valves if the force necessary exceeds the column strength of the catheter 14. Such a "pulling mode" is seen in FIG. 5.

Regardless of whether the assembly is placed through a "pushing mode" or a "pulling mode", normally the cutting fingers are enclosed by the sheath 14 until immediately prior to valve cutting. This enclosed condition is shown in phantom lines in FIG. 2 and in solid lines in FIG. 4. It assures that the cutting fingers will not dig into the walls of the vein through which the cutting assembly is passed.

The sheath 24 provides an annular conduit around the catheter 14 through which fluid may be injected into the vein. In use, pulsatile flow is applied through this passage to flutter the valves as the cutting assembly is passed through a vein so that the valves may be easily visually identified through the fiberoptic scope 22. Also, in the preferred use, pressure is so applied on a continuous basis to close a valve as it is being cut by the fingers 20. Such closing will automatically occur by applying reverse pressure to the valves.

The pulling mode, as seen in FIG. 5, is facilitated by a pulling loop 42 incorporated into the distal tip of the catheter 14. This loop is normally tucked away in a recessed section of the catheter and held in place with a circumferential band of shrinkable plastic tubing. When needed, the loop is taken out and extended forwardly of the cutting fingers 20. A pulling instrument, designated in its entirety by the numeral 44, is provided to apply tension to the catheter through the loop 42. This instrument, as will be described in more detail subsequently, is threaded through the vein in the direction of normal blood flow.

The pulling instrument 44, comprises a flexible catheter or sleeve 46 having a wire 48 extending therethrough. A third seal block 50 is sealingly secured to the sleeve 46 and contains an O-ring 52 disposed in sealed sliding engagement with the wire 48. A side branch conduit 54 is incorporated into the block 50 to provide an infusion port 56 in fluid communication with the annular passage defined between the sleeve 46 and the wire 48. This port provides means whereby fluid pressure may be applied to a vein through the pulling instrument.

The proximal end of the wire 48 has a control knob 58 secured thereto. The distal end of the wire is folded over at 60 to provide a hook which may be extended over the pulling loop 42. In use, the folded-over distal end 60 is extended out of the sleeve 46 so that it may be hooked over the loop and then drawn back into the sleeve, as shown in FIG. 5. Thus, the loop is secured in place and the distal end of the wire is shielded from contact with a vein within which the instrument 44 is used.

In the "pulling mode" the pulling instrument is placed within the vein to be treated in advance of securing the cutter assembly to the instrument. This is achieved by directing the catheter 46 fully through the vein in the normal direction of blood flow and then exiting the distal end of the catheter from a proximal venotomy. During such placement, the folded end of the wire 48 is retracted within the catheter. Upon exiting from the proximal venotomy, the wire is advanced forward by means of the knob 58 and the folded-over end is hooked around the loop 42. The folded-over end is then drawn into the catheter and the pulling instrument is then retracted to draw the cutter assembly into the vein, as seen in FIG. 5. The cutting operation is then carried out by the same process used in the "pushing mode"; the only difference being that the cutter assembly is drawn through the vein by a pulling force exerted through the pulling instrument, or a combination of pulling force exerted through the instrument and pushing force exerted through the cutter assembly.

As an alternative to the embodiments illustrated and described above, the cutting fingers 28 may be bonded directly to the outside cover of the fiberoptic scope 22, instead of requiring a separate catheter 14. The fiberoptic scope would then not be movable relative to the cutting fingers 28, and the second seal block 32 would not be required. The sheath 24 and first O-ring seal 26 would remain as before, as would the operation, except for movement of the scope relative to the catheter 14. This embodiment reduces the overall diameter of the cutter.

Conclusion

From the foregoing description, it is believed apparent that the present invention enables the attainment of the objects initially set forth herein. In particular, it provides an in-situ vein valve cutting apparatus and method wherein the cutting operation may be visually observed and avulsion of side branches and endothelial damage may be avoided. It should be understood, however, that the invention is not intended to be limited to the specifics of the preferred embodiments, but rather is defined by the accompanying claims.

We claim:

1. An improved in-situ vein valve cutter assembly comprising: an elongate flexible catheter having a through lumen and an open distal end; a plurality of cutter fingers secured at annularly spaced locations around the distal end of said catheter and extending generally longitudinally from said end; a viewing scope extending longitudinally through the lumen of said catheter to view through the open distal end thereof; and a tubular sheath telescopically received around said catheter, said sheath having an open distal end and being movable relative to said catheter to selectively confine the fingers within the sheath or extend the fingers from the open distal end of the sheath, said catheter and sheath being fabricated of material capable of bending to conform to the shape of a vein through which the assembly is directed.

2. A vein valve cutter assembly according to claim 1 wherein said fingers have proximal ends secured to the distal end of said catheter and distal ends which converge toward one another.

3. A vein valve cutter assembly according to claim 2 wherein said fingers diverge intermediate said proximal and distal ends.

4. A vein valve cutter assembly according to claim 1 wherein there are four of said cutter fingers disposed at equally spaced intervals around the distal end of said catheter.

5. A vein valve cutter assembly according to claim 1 further comprising: sheath seal means spaced from the distal end of the sheath to prevent fluid flow between the catheter and the sheath; and infusion means disposed intermediate said seal means and the distal end of the sheath to introduce fluid under pressure into said sheath.

6. A vein valve cutter assembly according to claim 1 wherein said viewing scope is telescopically received within the lumen of the catheter for select longitudinal movement relative to the catheter.

7. A vein valve cutter assembly according to claim 6 further comprising scope seal means to prevent fluid flow between the scope and catheter.

8. A vein valve cutter assembly according to claim 1 wherein said cutter fingers have inwardly directed knife edges.

9. A vein valve cutter assembly according to claim 1 further comprising a pull-line assembly secured to the distal end of said catheter.

10. A vein valve cutter assembly according to claim 9 wherein said pull-line assembly comprises: a loop secured to the distal end of said catheter; an elongated wire having a folded end hooked over said loop; and a sleeve received around said wire, said sleeve having an open end and being movable relative to the wire to selectively confine the folded end within the sleeve or extend the folded end through said open end.

11. A vein valve cutter assembly according to claim 10 further comprising wire seal means spaced from the open end of the sleeve to prevent fluid flow between the wire and sleeve.

12. A vein valve cutter assembly according to claim 11 further comprising secondary infusion means disposed intermediate said seal means and the open end of the sleeve to introduce fluid under pressure into the sleeve.

13. A vein valve cutter assembly comprising: a flexible elongate element having a distal end; a plurality of cutter fingers secured at annularly spaced locations around the distal end of said element; and a tubular sheath telescopically received around said element, said sheath having an open distal end and being movable relative to said element to selectively confine the fingers within the sheath or extend the fingers from the open distal end of the sheath, said element and sheath being fabricated of material capable of bending to conform to the shape of a vein through which the assembly is directed.

14. A vein valve cutter assembly according to claim 13 wherein said fingers extend from the distal end of the element, have proximal ends secured to the distal end of the element, and distal ends spaced from the distal end of the element and converging toward one another.

15. A vein valve cutter assembly according to claim 14 wherein said fingers diverge intermediate said proximal and distal ends.

16. A vein valve cutter assembly according to claim 13 wherein there are four of said cutter fingers disposed at equally spaced intervals around the distal end of the said element.

* * * * *